(12) United States Patent
Zal et al.

(10) Patent No.: US 9,220,929 B2
(45) Date of Patent: Dec. 29, 2015

(54) USE OF A HAEMOGLOBIN FOR THE PREPARATION OF DRESSINGS AND RESULTING DRESSINGS

(75) Inventors: Franck Zal, Morlaix-Ploujean (FR); Morgane Rousselot, Saint-Pol de Leon (FR)

(73) Assignees: CENTRE NATIONAL DE LA RECHERCHE SCIENTIFIQUE CNRS, Paris (FR); Hemarina, Morlax (FR); UNIVERSITE PIERRE ET MARIE CURE, Paris (FR)

( * ) Notice: Subject to any disclaimer, the term of this patent is extended or adjusted under 35 U.S.C. 154(b) by 567 days.

(21) Appl. No.: 12/665,589

(22) PCT Filed: Jun. 10, 2008

(86) PCT No.: PCT/FR2008/000786
§ 371 (c)(1),
(2), (4) Date: Jul. 20, 2010

(87) PCT Pub. No.: WO2009/007532
PCT Pub. Date: Jan. 15, 2009

(65) Prior Publication Data
US 2010/0278887 A1    Nov. 4, 2010

(30) Foreign Application Priority Data
Jun. 18, 2007  (FR) .................................... 07 04312

(51) Int. Cl.
| A61K 9/70 | (2006.01) |
| A61K 38/42 | (2006.01) |
| A61K 9/00 | (2006.01) |
| A61K 8/02 | (2006.01) |
| A61K 8/64 | (2006.01) |
| A61P 17/02 | (2006.01) |
| A61P 9/10 | (2006.01) |
| A61Q 19/08 | (2006.01) |
| A61Q 19/00 | (2006.01) |
| A61K 8/73 | (2006.01) |
| A61L 15/28 | (2006.01) |

(Continued)

(52) U.S. Cl.
CPC . *A61Q 19/00* (2013.01); *A61K 8/64* (2013.01); *A61K 8/73* (2013.01); *A61K 8/731* (2013.01); *A61K 8/733* (2013.01); *A61K 8/736* (2013.01); *A61K 38/42* (2013.01); *A61L 15/28* (2013.01); *A61L 15/44* (2013.01); *A61L 26/0023* (2013.01); *A61L 26/0066* (2013.01); *A61L 2300/252* (2013.01)

(58) Field of Classification Search
CPC ...................................................... A61K 38/42
See application file for complete search history.

(56) References Cited

U.S. PATENT DOCUMENTS

| 4,923,645 A * | 5/1990 | Tsang et al. | .................... 264/4.3 |
| 4,959,341 A | 9/1990 | Wallach | |
| 5,234,903 A * | 8/1993 | Nho et al. | .................... 514/13.4 |

(Continued)

OTHER PUBLICATIONS

Entrapment in Calcium Alginate by Fraser et al., from the book titlted Immobilization of Enzymes and Cells (1997).*

(Continued)

*Primary Examiner* — Scott Long
*Assistant Examiner* — Sarah Alawadi
(74) *Attorney, Agent, or Firm* — McDonnell Boehnen Hulbert & Berghoff

(57) ABSTRACT

The invention relates to the use of a haemoglobin for the preparation of dressings and to the resulting dressings.

7 Claims, 13 Drawing Sheets

(51) Int. Cl.
*A61L 15/44* (2006.01)
*A61L 26/00* (2006.01)

(56) References Cited

U.S. PATENT DOCUMENTS

| | | | | |
|---|---|---|---|---|
| 6,303,290 | B1* | 10/2001 | Liu et al. | 435/4 |
| 7,413,781 | B2* | 8/2008 | Hubbell et al. | 427/512 |
| 2003/0180365 | A1* | 9/2003 | Barnikol | 424/487 |
| 2004/0022839 | A1 | 2/2004 | Barnikol | |
| 2004/0086493 | A1 | 5/2004 | Hubbel | |
| 2005/0054595 | A1* | 3/2005 | Binette et al. | 514/44 |
| 2006/0134186 | A1 | 6/2006 | Carlton | |
| 2006/0223965 | A1* | 10/2006 | Trifu | 528/35 |

OTHER PUBLICATIONS

Rousselot et al. Arenicola marina extracellular hemoglobin: a new promising blood substitute: Biotechnol J. Feb. 2006.*

* cited by examiner

USE OF A HAEMOGLOBIN FOR THE PREPARATION OF DRESSINGS AND RESULTING DRESSINGS

The present invention relates to the use of a hemoglobin for the preparation of dressings and to the resulting dressings.

Hemoglobin present in the human or animal bloodstream transports oxygen from the lungs to the extremities of the limbs. Oxygen has a very low solubility in an aqueous medium, and is therefore distributed in the organism, very close to the cells, via hemoglobin by virtue of the capillary network, by diffusion.

When there is an open injury to the skin, the supply of oxygen by diffusion at the surface of cells is then eliminated.

The skin is a complex tissue which provides elementary protection, sensitivity, thermoregulation and metabolism functions. An interruption in tissue continuity (wound) can have an effect on each of these functions.

A distinction can be made between two types of wounds, depending on the healing time: acute wounds and chronic wounds. The healing of the first occurs without complication and in less than six weeks. The second are defined as skin lesions for which the healing time is more than six weeks.

Chronic wounds group together, inter alia, decubitus ulcers, leg ulcers and "diabetic foot" ulcers.

The decubitus ulcer is a skin lesion of ischemic origin linked to a compression of the soft tissues between a hard surface and bone projections.

The leg ulcer is a wound located below the knee, which has not spontaneously healed, and which is in general of venous origin.

The "diabetic foot" is a consequence of vascular and neurological complications with diabetes, in the feet. These wounds are all directly or indirectly linked to a problem of oxygenation.

For example, in the case of decubitus ulcers, the compression leads to a reduction in blood supply and therefore in $O_2$ supply (hypoxia) and in nutrient supply at the cellular level, which results in ischemia and then in necrosis. The compression creates a venous obstruction and therefore a stasis, followed by obstruction of the capillaries and then of the musculocutaneous arteries.

The ischemia (decrease in blood circulation) results essentially from the attack on the vascular system. This results in a reduction in the amounts of $O_2$ and of nutrients which is responsible for the delay in wound healing. Infection may be superficial, but the risk thereof is linked to deep involvement that may threaten the tissues, sheaths and tendons, and especially the bone structures.

Periodontal diseases are also very common in diabetic patients. Very often, the immune system of these patients does not make it possible to effectively confront a bacterial infection. At the oral level, there follows an imbalance in the oral flora with a proliferation of anaerobic pathogens.

Numerous external factors are also responsible for this pathological condition, which most of the time is due to a proliferation of anaerobic bacteria.

In order to promote healing, and in particular that of chronic open wounds, several techniques have been developed over the past few years, and in particular the use of hemoglobin alone or in combination with a gel.

Thus, patent EP 0 862 440 describes the therapeutic use of hemoglobin of any type for promoting healing in a patient. The hemoglobin is administered intravenously and may be natural or chemically modified. However, there are two problems with using natural hemoglobin: firstly, its instability over time and, secondly, the possibility of triggering an allergic reaction in the patient.

Patent application US 2003/0180365 concerns an externally applicable preparation containing an oxygen carrier, in which the oxygen carrier is incorporated into, and molecularly dispersed in, a preparation having the consistency of a gel, for regeneration of the skin in the case of oxygen deficiency.

The gel used may be an inorganic gel or an organic gel. The oxygen carrier may be human or animal native hemoglobin or a mixture of said hemoglobin with a horse, dog or sheep myoglobin.

This gel releases the oxygen-transporting hemoglobin in the skin so as to allow diffusion of the oxygen in the epidermis. This gel does not have bactericidal properties and cannot therefore be used in the context of open wounds having too great an exudate, since there is then a need to combat the infection present in the exudate.

Preferably, the hemoglobin is protected from oxidation, i.e. stabilized, in particular with CO. It is specified in this document that hemoglobin can be used without stabilization, but that such a preparation cannot be stored for as long as the stabilized preparation, because of the oxidation of the hemoglobin.

Application US 2004/0022839 describes an externally applicable formulation containing an oxygen carrier, in which the oxygen carrier is incorporated into a lipoid emulsion.

This formulation is intended for skin regeneration in the event of oxygen deficiency and also cannot be used for the treatment of open wounds.

The oxygen carrier may be hemoglobin and the formulation releases the oxygen-transporting hemoglobin in the skin so as to allow diffusion of the oxygen in the epidermis.

The same problems as previously are encountered with this formulation, namely oxidation of the hemoglobin, if the latter is not stabilized with an antioxidant, and the need to use natural cofactors such as 2,3-diphosphoglycerate, or non-natural cofactors such as inositol hexaphosphate or mellitic acid, in order to obtain an action on epidermal regeneration.

Application US 2005/0129747 describes the use of an optionally modified oxygen carrier for the production of an agent for the external treatment of open wounds.

The oxygen carrier may be an optionally modified hemoglobin or myoglobin of human or animal origin, and the carrier is used in a solution or by spraying.

The hemoglobin thus deposited in the aqueous barrier of the open wound enables the oxygen to diffuse through this barrier so as to promote healing.

The limitations of this carrier lie in the oxidation of the native hemoglobin and, consequently, the need to use antioxidants, cofactors or chemically modified hemoglobin.

Application US 2005/0232953 describes water-in-oil microemulsions comprising an optionally modified hemoglobin and also antioxidants.

It is specified in this application that the vital cells of the epithelium of the skin are protected from the external environment by the stratum corneum, which is difficult to penetrate. Consequently, the two conditions, according to this application, for an active substance to bypass the stratum corneum barrier are the following:
1) penetration: entry of the substance into the stratum corneum,
2) permeation: diffusion of the substance from the stratum corneum to the epidermis.

According to this application, the hemoglobin contained in the microemulsion penetrates rapidly and deeply into the stratum corneum and diffuses the oxygen therein.

However, this hemoglobin will rapidly oxidize in the stratum corneum and consequently requires the presence of an antioxidant, since it is well known that, when a hemoglobin is isolated from red blood cells, said hemoglobin will become oxidized due to the absence of the anti-oxidizing activity of the enzymes present in the red blood cells (Savitsky J P, Doczi J, Black J Arnold J D (1978) A clinical safety trial of stroma-free hemoglobin. Clin Pharmacol Ther 23, 73-80), (Chan W L, Tang N L, Yim C C, Lai F M & Tam M S (2000); New features of renal lesion induced by stroma free hemoglobin, Toxicol Pathol 28, 635-642).

Consequently, one of the objects of the invention is to provide a dressing containing hemoglobin which is immobilized and stable in a matrix allowing the treatment of ischemic wounds.

Another object of the invention is to provide a dressing based on hemoglobin which does not require the use of cofactors or of antioxidants.

Another aspect of the invention is to provide a dressing based on hemoglobin which allows sustained use over time and avoids the triggering of allergic reactions.

Another object of the invention is to provide cosmetic or pharmaceutical compositions comprising hemoglobin in a matrix for the treatment of ischemic wounds and/or of local infections caused by pathogens, in particular anaerobic pathogens.

Another object of the invention is to provide a method for preparing hemoglobin immobilized in a matrix.

Consequently, the invention relates to the use of a human hemoglobin or a hemoglobin from a vertebrate or invertebrate animal, which is essentially immobilized in a matrix and stable in the matrix, said matrix being physiologically acceptable and based on advantageously polymerized hydrocolloids, and having a water content of 0 to 98%, as an oxygen carrier in a physiological tissue, in particular a hypoxic tissue, requiring an oxygen supply, without the release of the hemoglobin essentially immobilized in the abovementioned matrix being greater than 10% by weight.

The expression "hemoglobin essentially immobilized in a matrix" should be understood to mean that the hemoglobin remains in the matrix and is virtually not released, i.e. freed out of said matrix.

The proportion of hemoglobin released is measured under simulated in vivo conditions by colorimetric assay using Drabkin's reagent as explained in example 5.

The expression "stable in the matrix" means that the hemoglobin is not oxidized in the matrix and that it does not denature.

In particular, the dressing of the invention does not become liquefied on contact with the wound, thus avoiding release of the hemoglobin.

The matrix represents the medium in which the hemoglobin is immobilized and is constituted of hydrocolloids, i.e. an attachment agent of plant origin.

Therefore, the hemoglobin thus trapped in the matrix does not enter into the skin, whether into the stratum corneum or into the epidermis, which will thus allow continual diffusion of the oxygen in the stratum corneum.

The term "vertebrate animal" denotes a bovine, a mammal such as a pig, a sheep, a monkey or a snake, and the term "invertebrate animal" denotes an insect, or an animal belonging to the branch of the annelids.

The term "hypoxic" physiological tissue denotes a tissue that is low in oxygen or has a reduced oxygen level (for example, when the tissue denotes a wound, the transcutaneous partial pressure of $O_2$ is less than 40 mmHg; Smith B, Devigne L, Slade J, Dooley J & Warren D. Wound Rep Reg. 4, 224 (1996)).

The hemoglobin immobilized in a matrix constitutes a dressing, this being a term which may subsequently be used to denote said hemoglobin immobilized in a matrix.

The matrix contains from 0 to 98% of water since it may be in a dry form, i.e. containing from 0 to 5% of water, or in a wet form, i.e. containing from 50% to 98% of water.

In one preferred embodiment, the invention relates to the use of a hemoglobin immobilized in a matrix, as defined above, for the preparation of a dressing intended for the external treatment of open, deep or chronic wounds, or of periodontal diseases, or for the preparation of a pharmaceutical composition intended for a gastric dressing or for the preparation of cosmetic compositions.

The open wounds are lesions caused by an external agent and which lead to an opening of the skin.

The deep wounds are wounds in which the muscles and then the bones or organs may be affected.

The chronic wounds group together in particular decubitus ulcers, leg ulcers and diabetic foot ulcers (FIG. 1).

The periodontal diseases concern all the support tissues for the teeth: the gum (FIG. 2), the ligament and the alveolar bone.

The term "gastric dressing" should be understood to mean a dressing capable of forming a film-coating protecting the gastric mucosa and making it possible to thus act as a gastric protector for the treatment in particular of gastritis, of esophageal burns or of meteorism.

The cosmetic compositions are intended for skin regeneration in the case of oxygen deficiency or for the prevention of this deficiency, and in particular in the context of degenerative modifications of the skin, or of modifications induced by radiation, by heat or by age, and in particular wrinkles.

According to another embodiment, the invention relates to the use of a hemoglobin immobilized in a matrix as defined above, in which the matrix is formed from a three-dimensional network defining pores the size of which is from approximately 2 nm to approximately 300 µm, preferentially from approximately 2 nm to approximately 10 µm, preferentially from approximately 2 nm to approximately 1 µm, even more preferentially from approximately 5 nm to approximately 200 nm, and preferentially of approximately 15 nm.

The size of the pores is advantageously 15 nm so as to be able to contain the hemoglobin.

The pores are represented in FIG. 4. There are two types of pores in the matrix, large pores measuring approximately 150 µm and much smaller pores, of the order of about ten nanometers, and containing the hemoglobin. These pores are located in the membranes surrounding the large pores and contain the hemoglobin.

In one preferred embodiment, in the use of the hemoglobin stabilized in the matrix, the amount of hemoglobin relative to the total dry weight of hemoglobin and of matrix is from approximately 0.1% (w/w) to approximately 60% (w/w), preferentially from approximately 10% (w/w) to approximately 50% (w/w), preferentially from approximately 15% (w/w) to approximately 45% (w/w), preferentially from approximately 30% (w/w) to approximately 40% (w/w), and more preferentially approximately 40% (w/w).

The amount of hemoglobin is herein indicated by dry weight.

If the amount of hemoglobin is less than 0.1%, the oxygen transport will no longer be efficient.

If the amount of hemoglobin is greater than 60%, the dressing then releases too much hemoglobin.

An amount of hemoglobin of 40% makes it possible to have the best compromise between oxygen transport efficiency and less release.

According to one advantageous embodiment, the invention relates to the use of a hemoglobin immobilized in a matrix, as defined above, in which the percentage water content is from 0% to approximately 98%, and preferentially approximately 50%.

A percentage water content of 50% represents the best compromise between low release, oxygen transport efficiency and ease of handling of the dressing.

According to one preferred embodiment of the invention, the hemoglobin is chemically modified or crosslinked human or vertebrate-animal hemoglobin.

The vertebrate-animal hemoglobin may be a bovine hemoglobin, or a hemoglobin from a mammal such as a pig, a sheep, a monkey or a serpent.

The hemoglobin may be chemically modified for example with CO so as to obtain a carboxyhemoglobin.

The hemoglobin may be crosslinked by creating a chemical bridge between two of its four polypeptide chains and by linking several hemoglobin molecules together according to the techniques known in the literature (J. M. Harris (editor): Poly-ethylene glycol chemistry: Biotechnical and Biomedical Application, Plenum, N.Y. et al. 1992).

The crosslinking agents used may be polypropylene glycols or polyethylene glycols or dialdehydes.

In one preferred embodiment of the invention, the hemoglobin is an extracellular hemoglobin from an invertebrate animal, chosen from the phylum Annelida, and is in particular an extracellular hemoglobin belonging to marine worms such as *Arenicola marina*.

In the phylum Annelida, a distinction is made between three classes: the polychaetes (such as *Arenicola marina*), the oligochaetes (such as the earthworm *Lumbricus terrestris*) and the achaetes (such as leeches).

Annelids are segmented protostome animals (having metamers, sometimes a very large number of metamers) in the form of a "worm". They live essentially in water (seawater, such as Nereis, or freshwater, such as the leech), even though some species, such as the earthworms, live in the soil.

The use of an extracellular hemoglobin which is stable in the matrix makes it possible to avoid the use of an antioxidant and/or of a cofactor in order to function.

The use of an extracellular hemoglobin which is stable in the matrix makes it possible to involve the intrinsic SOD activity (determined by the method of Flohé & Ötting; Flohé L, Otting F, Methods Enzymol (1984), 105, 93-104) of said hemoglobin, thus providing it with an intrinsic antioxidizing activity, and consequently requiring no antioxidant or cofactor in order to function.

According to one advantageous embodiment of the invention, said matrix is based on chitosan, carrageenans, carboxymethylcellulose or alginates, and in particular sodium alginate or calcium alginate.

The calcium alginate may be obtained by sodium alginate ion exchange, by reaction of sodium alginate with a divalent cation such as calcium chloride, calcium acetate, calcium carbonate or calcium phosphate, preferably calcium chloride.

The chitosan is produced by deacetylation of the chitin present in the exoskeleton of insects and other arthropods (crustaceans, arachnids, etc).

It is an aminopolysaccharide constituted of N-acetyl-D-glucose-2-amine groups linked to one another by a β-(1,4) linkage.

Carrageenans are linear polysaccharides constituted of more or less substituted galactose molecules. The chain is constituted of subunits, called carrabioses, comprising two galactoses linked via a β-(1,4) linkage. These carrabioses are linked to one another in the chain by α-(1,3) linkages.

Carboxymethylcellulose is a polymer derived from natural cellulose, formed by reaction of cellulose with a base and chloroacetic acid. It is based on a β-(1,4)-D-glucopyranose structure.

Alginates are polymers of alginic acid (constituted of mannuronic acid and of guluronic acid) obtained from brown algae (Laminariales, Fucales). The sodium alginate is extracted from the algae with sodium hydroxide and then dried so as to obtain a white powder, having a molecular weight ranging from 32 000 to 200 000 Da.

In one preferred embodiment of the invention, the ratio of said alginate to the total weight of hemoglobin and of matrix is from approximately 40% (w/w) to approximately 99% (w/w), preferentially from approximately 50% (w/w) to approximately 90% (w/w), preferentially from approximately 55% (w/w) to approximately 85% (w/w), preferentially from approximately 60% (w/w) to approximately 80% (w/w), and preferentially approximately 60% (w/w).

The amount of alginate used herein is indicated as dry weight.

If the ratio is less than 40%, release of the hemoglobin is then observed.

If the ratio is greater than 60%, the oxygen transport efficiency is reduced.

According to one advantageous embodiment, the invention relates to the use of a hemoglobin immobilized in a matrix, as defined above, which allows the creation of an oxygen gradient through the gel, toward the oxygen-deficient zone.

One of the advantages of the invention lies in the immobilization of the hemoglobin in the matrix with less than 10% release.

This immobilization allows oxygen from the air to be fixed by the hemoglobin through the gel and then the oxygen to be released in the wound, thus resulting in the creation of an oxygen gradient.

By way of example, the affinity of the *Arenicola marina* hemoglobin in the dressing is $P_{50}=7-8$ (the $P_{50}$ is the $PO_2$ for which 50% of the *Arenicola marina* hemoglobin is saturated with $O_2$), i.e. the matrix fixes oxygen from the air if the $PO_2$ is greater than 8 and releases it if the $PO_2$ is less than 7 (FIG. 5).

In one preferred embodiment of the invention, the hemoglobin is in combination with one or more elements chosen from cofactors, preservatives such as methyl 4-hydroxybenzoate or propyl 4-hydroxybenzoate, antioxidants such as reduced glutathione, ascorbic acid, NADH, human myoglobin or myoglobin of animal origin, or a combination of these elements.

Although the hemoglobin of the invention can function without antioxidants or cofactors, it may be advantageous, if necessary, in order to further increase the lifetime of the dressing, to add antioxidants or preservatives, or cofactors and/or myoglobin, which make it possible to optimize the functioning of the dressing.

According to one advantageous embodiment, the use of a hemoglobin immobilized in a matrix, according to the invention, makes it possible to exert a bactericidal effect on Gram-anaerobic bacteria.

In the context of periodontal diseases (FIG. 2), it is anaerobic bacteria, which are the most pathogenic, that are responsible for the pathological condition (table 1).

These pathogens, which are highly refractory to antibiotic treatments, cause pockets between the gum and the tooth which can lead to bone lesions and loss of the tooth organ.

TABLE 1

List of pathogens responsible for periodontal diseases. Most of these bacteria are anaerobic microorganisms.

| | CG | PPP | LJP | GJP | RPP | AP | SAP | TAP | RP | HIV-P | NUG |
|---|---|---|---|---|---|---|---|---|---|---|---|
| *Actinobacillus actinomycetemcomitans* | | + | +++ | | | + | ++ | | | + | |
| *Eikenella corrodens* | ++ | + | | | + | + | | | | + | |
| Capnocytopaga species | ++ | | | | + | + | | | | + | |
| *Porphyromanas gingivalis* | | + | | ++ | +++ | + | | | | + | |
| *Prevotella intermedia* | + | + | + | | | + | ++ | ++ | ++ | + | +++ |
| *Bacteroides forsythus* | | | | | | + | | | | + | |
| *Prevotella melanogenica* | | | | | | + | | | | + | |
| *Fusobacterium nucleatum* | ++ | + | | | | + | | | ++ | + | + |
| *Campylobacter rectus* | + | | | | | + | | | | +++ | |
| *Peptostreptococcus micros* | | | | | | + | | | | + | |
| Treponema species | | | | | + | + | ++ | | + | ++ | +++ |
| Enterobacteria | | | | | | | | | + | + | |
| Aero-anaerobic Gr+ bacteria | +++ | | | | | | | | | | |

CG = chronic gingivitis (or plaque-associated gingivitis),
PPP = prepubertal periodontitis,
LJP = localized juvenile periodontitis (or aggressive periodontitis),
GJP = generalized juvenile periodontitis (or aggressive periodontitis),
RPP = rapidly progressive periodontitis (or aggressive periodontitis),
AP = adult periodontitis (or localized/generalized chronic periodontitis),
SAP = active phase of adult periodontitis (or aggressive periodontitis),
TAP = tobacco-associated periodontitis (or aggressive periodontitis),
RP = refractory periodontitis,
HIV-P = HIV-associated periodontitis (necrotizing periodontitis),
NUG = necrotizing ulcerative gingivitis (necrotizing periodontitis).
Frequency of isolation of pathogenic bacteria: +, ++, +++.

In fact, when a wound exhibits an exudate, the latter contains bacteria which cause an infection and it is then necessary to combat both the exudate and the infection.

The dressing of the invention consequently makes it possible to combat the infection by draining the exudate; the oxygen then present in the dressing can exert its bactericidal activity, and the oxygen gradient created promotes healing.

In another aspect, the invention relates to a dressing comprising a human hemoglobin or a hemoglobin from a vertebrate or invertebrate animal, which is essentially immobilized in a matrix and stable in the matrix, said matrix being physiologically acceptable and based on physiologically compatible hydrocolloids, having a water content of from 0% to 98%, and releasing the hemoglobin contained in the above-mentioned matrix only in a proportion of less than 10%.

The dressing requires the presence of a water content in order to function; however, a dressing having a very low water content (less than 5% of water) is advantageous since it makes it possible to increase the storage time.

The dressing defined above may be in the liquid or dry form.

According to one advantageous embodiment, the invention relates to a dressing comprising a hemoglobin immobilized in a matrix, as defined above, in which said matrix is formed from a three-dimensional network defining pores, the size of which is from approximately 2 nm to approximately 300 µm, preferentially from approximately 2 nm to approximately 10 µm, preferentially from approximately 2 nm to approximately 1 µm, even more preferentially from approximately 5 nm to approximately 200 µm, and preferentially approximately 15 nm.

The dressing defined above may be in the liquid or dry form.

In another embodiment, the invention relates to a dressing comprising a hemoglobin immobilized in a matrix, as defined above, in which the amount of hemoglobin relative to the total dry weight of hemoglobin and of matrix is from approximately 0.1% (w/w) to approximately 60% (w/w), preferentially from approximately 10% (w/w) to approximately 50% (w/w), preferentially from approximately 15% (w/w) to approximately 45% (w/w), preferentially from approximately 30% (w/w) to approximately 40% (w/w), and more preferentially approximately 40% (w/w).

The amount of hemoglobin indicated herein corresponds to the dry weight of hemoglobin.

The dressing defined above may be in the liquid or dry form.

According to one advantageous embodiment, the invention relates to a dressing comprising a hemoglobin immobilized in a matrix, as defined above, in which the percentage water content is greater than approximately 50% and remaining from approximately 50% to approximately 98%, preferentially approximately 95%.

The dressing requires the presence of a water content in order to function, otherwise the oxygen gradient cannot be created.

The dressing defined above will be denoted liquid-form dressing.

In another embodiment, the invention relates to a dressing comprising a hemoglobin immobilized in a matrix, as defined above, in which the percentage water content is less than approximately 5% and remaining from approximately 5% to approximately 0%, preferentially approximately 2%.

The dressing advantageously contains no water or a very small amount (less than 5% of water), thus allowing prolonged storage thereof and therefore an extended storage time compared with the wet form. In order for the dressing to be functional, it is sufficient to rehydrate it.

The dressing defined above will be denoted dry-form dressing.

According to one advantageous embodiment, the invention relates to a dressing comprising a hemoglobin immobilized in a matrix, as defined above, in which the hemoglobin is chemically modified or crosslinked human or vertebrate-animal hemoglobin.

The dressing defined above may be in the liquid or dry form.

According to another embodiment, the invention relates to a dressing comprising a hemoglobin immobilized in a matrix, as defined above, in which the hemoglobin is an extracellular hemoglobin from an invertebrate animal, chosen from the phylum Annelida, and in particular an extracellular hemoglobin belonging to marine worms such as *Arenicola marina*.

The dressing defined above may be in the liquid or dry form.

In another embodiment, the invention relates to a dressing comprising a hemoglobin immobilized in a matrix, as defined above, in which said matrix is based on chitosan, carrageenans, carboxymethylcellulose or alginates, and in particular sodium alginate or calcium alginate.

The calcium alginate can be obtained by sodium alginate ion exchange, by reaction of sodium alginate with a divalent cation such as calcium chloride, calcium acetate, calcium carbonate or calcium phosphate, preferably calcium chloride.

The dressing defined above may be in the liquid or dry form.

According to one advantageous embodiment, the invention relates to a dressing comprising a hemoglobin immobilized in a matrix, as defined above, in which said alginate, relative to the total dry weight of hemoglobin and of matrix, is present in a proportion of from approximately 40% (w/w) to approximately 99% (w/w), preferentially from approximately 50% (w/w) to approximately 90% (w/w), preferentially from approximately 55% (w/w) to approximately 85% (w/w), preferentially from approximately 60% (w/w) to approximately 80% (w/w), and preferentially approximately 60% (w/w).

The dressing defined above may be in the liquid or dry form.

According to one advantageous embodiment, the invention relates to a dressing comprising a hemoglobin immobilized in a matrix, as defined above, which allows the creation of an oxygen gradient through the gel, from the oxygenated zone to the hypoxic zone.

The oxygenated zone is the external part of the dressing in contact with the ambient air, this being the part that will capture the oxygen from the air.

The hypoxic zone is the part in contact with the wound and which is deficient in oxygen.

In another embodiment, the invention relates to a dressing comprising a hemoglobin immobilized in a matrix, as defined above, in which the hemoglobin is in combination with one or more elements chosen from cofactors, preservatives such as methyl 4-hydroxy-benzoate or propyl 4-hydroxybenzoate, antioxidants such as reduced glutathione, ascorbic acid, NADH, human myoglobin or myoglobin of animal origin, or a combination of these elements.

The dressing defined above may be in the liquid or dry form.

According to one advantageous embodiment, the invention relates to a dressing comprising a hemoglobin immobilized in a matrix, as defined above, which has a bactericidal effect on anaerobic Gram-bacteria.

The dressing defined above may be in the liquid or dry form.

According to yet another aspect, the invention relates to an intermediate composition in aqueous form, comprising a mixture of a human hemoglobin or a hemoglobin from a vertebrate or invertebrate animal and of a nonpolymerized hydrocolloid, which is physiologically acceptable, in solution, in particular in water, or in a physiologically compatible buffer.

The intermediate composition defined above will be denoted liquid intermediate composition.

The hydrocolloid is nonpolymerized, i.e. it is an attachment agent of plant origin, composed of polysaccharides and capable of forming a gel, and chosen from chitosan, carrageenans, carboxymethyl-cellulose or alginates, such as potassium alginate, lithium alginate, magnesium alginate or ammonium alginate, and preferably sodium alginate.

According to another aspect, the invention relates to an intermediate composition in dried form, having a water content of less than 5%, comprising a mixture of a human hemoglobin or a hemoglobin from a vertebrate or invertebrate animal and of a physiologically acceptable hydrocolloid.

The intermediate composition defined above will be denoted dry intermediate composition.

The hydrocolloid is nonpolymerized, as defined above.

According to one advantageous embodiment, the invention relates to an intermediate composition as defined above, in which the amount of hemoglobin, relative to the total weight of hemoglobin and of hydrocolloid, is from approximately 0.1% (w/w) to approximately 60% (w/w), preferentially from approximately 10% (w/w) to approximately 50% (w/w), preferentially from approximately 15% (w/w) to approximately 45% (w/w), preferentially from approximately 30% (w/w) to approximately 40% (w/w), and more preferentially approximately 40% (w/w).

The amount of hemoglobin indicated herein is in dry weight.

The intermediate composition defined above may be in the liquid or dry form.

According to one advantageous embodiment, the invention relates to an intermediate composition as defined above, in which the hemoglobin is chemically modified or crosslinked human or vertebrate-animal hemoglobin.

The intermediate composition defined above may be in the liquid or dry form.

In another embodiment, the invention relates to an intermediate composition as defined above, in which the hemoglobin is an extracellular hemoglobin from an invertebrate animal, chosen from phylum Annelida, and in particular an extracellular hemoglobin belonging to marine worms such as *Arenicola marina*.

The intermediate composition defined above may be in the liquid or dry form.

According to one advantageous embodiment, the invention relates to an intermediate composition as defined above, in which the hydrocolloid is based on chitosan, carrageenans, carboxymethylcellulose or alginates, and in particular sodium alginate.

The intermediate composition defined above may be in the liquid or dry form.

In another embodiment, the invention relates to an intermediate composition as defined above, in which said alginate, relative to the total weight of hemoglobin and of hydrocolloids, is present in a proportion of from approximately 40% (w/w) to approximately 99% (w/w), preferentially from approximately 50% (w/w) to approximately 90% (w/w), preferentially from approximately 55% (w/w) to approximately 85% (w/w), preferentially from approximately 60% (w/w) to approximately 80% (w/w), and preferentially approximately 60% (w/w).

The intermediate composition defined above may be in the liquid or dry form.

The amount of alginate indicated herein is in dry weight.

According to one advantageous embodiment, the invention relates to an intermediate composition as defined above, in which the hemoglobin is in combination with one or more elements chosen from cofactors, preservatives such as methyl 4-hydroxybenzoate or propyl 4-hydroxybenzoate, antioxidants such as reduced glutathione, ascorbic acid, NADH, human myoglobin or myoglobin of animal origin, or a combination of these elements.

The intermediate composition defined above may be in the liquid or dry form.

According to yet another aspect, the invention relates to a pharmaceutical composition comprising, as active substance, a human hemoglobin or a hemoglobin from a vertebrate or invertebrate animal, which is essentially immobilized in a matrix and stable in the matrix, said matrix being physiologically acceptable, in combination with a pharmaceutically acceptable carrier.

According to one advantageous embodiment, the invention relates to a pharmaceutical composition as defined above which is in a form that can be administered topically at a rate of from 0.012 mg/d to 100 mg/d of active substance, preferentially from 0.12 mg/d to 100 mg/d, and more preferentially from 10 mg/d to 20 mg/d, or in a form that can be administered orally at a rate of from 0.012 mg/kg/d to 100 mg/kg/d of active substance, preferentially from 0.12 mg/kg/d to 100 mg/kg/d, and more preferentially from 10 mg/kg/d to 20 mg/kg/d.

The pharmaceutical compositions that can be administered topically are intended for the treatment of periodontal diseases which concern all the support tissues for the teeth: the gum (FIG. 2), the ligament and the alveolar bone, and those that can be administered orally are intended for protection of the gastric mucosa, as a gastric protector for the treatment in particular of gastritis, of esophageal burns or of meteorism.

According to yet another aspect, the invention relates to a cosmetic composition comprising a human hemoglobin or a hemoglobin from a vertebrate or invertebrate animal, which is essentially immobilized in a matrix and stable in the matrix, said matrix being physiologically acceptable, in combination with a cosmetically acceptable carrier.

According to one advantageous embodiment, the invention relates to a cosmetic composition as defined above, which is in a form that can be administered topically at a rate of from 0.012 mg/d to 100 mg/d of active substance, preferentially from 0.12 mg/d to 100 mg/d, and more preferentially from 10 mg/d to 20 mg/d.

The cosmetic compositions are intended for regeneration of the skin in the case of oxygen deficiency or for prevention of this deficiency, and in particular in the context of degenerative modifications of the skin, modifications induced by radiation, by heat or by age, and in particular wrinkles.

According to yet another aspect, the invention relates to a method for preparing a dressing constituted of a human hemoglobin or a hemoglobin from a vertebrate or invertebrate animal, which is essentially immobilized in a matrix based on hydrocolloid and having a water content of from 0% to 98%, comprising a step of polymerization of said hydrocolloid contained in a mixture of hydrocolloid and of a hemoglobin, which mixture has a water content of less than 5%, in an aqueous solution of a divalent or trivalent cation, or a solution containing a bridging agent such as dialdehydes.

The compound obtained corresponds to the dressing in wet form containing from 50% to 98% of water.

Given the instability of hemoglobin, it was not obvious for those skilled in the art that the polymerization of the hydrocolloid can be carried out in the presence of hemoglobin and makes it possible to obtain, as final product, a dressing which conserves all the functionalities thereof.

The aqueous solution of divalent or trivalent cation makes it possible to carry out the polymerization of the hydrocolloid by ion exchange with respect to the initial hydrocolloid.

The divalent or trivalent cations are chosen from calcium chloride, zinc acetate, calcium acetate, calcium carbonate, calcium phosphate, aluminum chloride and glutaraldehyde, preferably calcium chloride, and are used at a concentration of from 0.1% to 15%, preferentially from 2% to 10%, and more preferentially 10%.

According to one advantageous embodiment, the invention relates to a preparation method, as defined above, in which the mixture of the hydrocolloid and of a hemoglobin having a water content of less than 5% has been prepared by vacuum-drying an aqueous solution of a hydrocolloid and of the hemoglobin.

One of the advantages of the method is that the aqueous solution containing a hydrocolloid and a hemoglobin can be dried before polymerization, unlike the techniques normally used, where the drying occurs after the polymerization.

The drying before polymerization makes it possible to limit the release of the hemoglobin and to obtain a dressing of fine thickness.

Said aqueous solution was prepared by mixing an aqueous solution of a hydrocolloid at a concentration of from 1% to 3% with an aqueous solution of hemoglobin at a concentration of from 2 to 10 mg/ml.

According to one advantageous embodiment, the invention relates to a preparation method, as defined above, comprising a subsequent step of dehydration of a dressing having a water content of from approximately 50% to 98%, so as to obtain a dressing having a water content of less than 5%.

One of the advantages of the method which results in the dressing having a water content of less than 5% (dry form) lies in the fact that this dressing can be stored for a longer period of time than the wet form containing from 50% to 98% of water (wet form).

According to one advantageous embodiment, the invention relates to a preparation method, as defined above, comprising a subsequent step of rehydration of the dressing having a water content of less than 5%, so as to obtain a dressing having a water content of from approximately 40% to 70%.

The dressing having a water content of less than 5% (dry form), the storage product, can advantageously be subsequently rehydrated so as to be used in the same manner as the wet dressing (wet form) obtained directly.

According to one advantageous embodiment, the invention relates to a preparation method, as defined above, in which the extracellular hemoglobin from an invertebrate animal, chosen from the phylum Annelida, and in particular an extracellular hemoglobin belonging to marine worms such as *Arenicola marina*.

According to another embodiment, the invention relates to a preparation method, as defined above, in which the hydrocolloid is based on chitosan, carrageenans, carboxymethylcellulose or alginates, and in particular sodium alginate or calcium alginate.

According to one advantageous embodiment, the invention relates to a preparation method, as defined above, comprising the following steps:

a. mixing a solution containing a hemoglobin and a solution containing a hydrocolloid, the proportion of hemoglobin, relative to the total dry weight of hemoglobin and of hydrocolloid, being from approximately 0.1% (w/w) to approximately 60% (w/w), preferentially from approximately 10% (w/w) to approximately 50% (w/w), preferentially from approximately 15% (w/w) to approximately 45% (w/w), and more preferentially approximately 40% (w/w), so as to obtain an intermediate composition in aqueous form constituted of a mixture of hemoglobin and of a hydrocolloid in solution, b. vacuum-drying said mixture of hemoglobin and of a hydrocolloid in solution, so as to obtain a mixture of hemoglobin and of a hydrocolloid having a water content of less than 5%, c. polymerizing said hydrocolloid in said mixture having a water content of less than 5%, in an aqueous solution of a divalent cation chosen from calcium chloride, zinc acetate, calcium acetate, calcium carbonate, calcium phosphate, aluminum chloride or dialdehydes, and preferentially calcium chloride, at a concentration of from 0.1% to 5%, preferentially from 2% to 10%, and more preferentially 10%, so as to obtain a dressing having a water content of from 50% to 98%, d. optionally, dehydrating by evaporation under vacuum and/or lyophilizing said dressing having a water content of from 50% to 98%, so as to obtain a storage product having a water content of less than 5%, e. optionally, rehydrating said storage product having a water content of less than 5%, so as to obtain a dressing having a water content of from 40% to 70%.

According to another aspect, the invention relates to a dressing having a water content of from 0% to 98%, as obtained by means of the method defined above.

According to another aspect, the invention relates to a combination product containing an intermediate composition in aqueous form as defined above and an aqueous solution of a divalent or trivalent cation, or an aqueous solution containing a bridging agent such as dialdehydes, for producing a dressing having a water content of from 50% to 98%, by in situ polymerization of said hydrocolloid contained in said intermediate composition in said aqueous solution.

One of the advantages of the invention is to provide a dressing which can be produced in situ (FIG. 6), and which is in particular of use in the treatment of periodontal diseases, it being possible for the dressing to be applied directly in the buccal cavity, or for the treatment of deep wounds.

EXPERIMENTAL SECTION

Example 1

Purification of Hemoglobin from *Arenicola marina*

Figure 1:
FIG. 1 represents an example of a chronic wound: diabetic patient suffering from ischemia in the foot.
Figure 2:
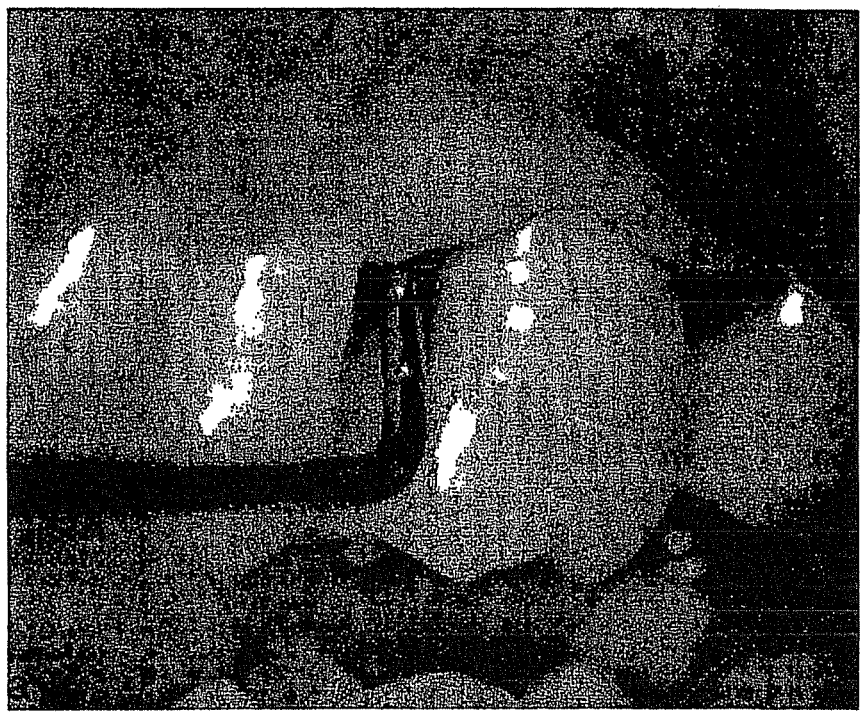
FIG. 2 represents an attack on the periodontium by anaerobic pathogens, creating pockets between the gum and the tooth organ.

The worms originate from a SeaBait breeding farm. These worms are frozen at −80° C., which causes a hemorrhagic shock and rupture of the wall of the worm; hemoglobin extraction is thus facilitated.

The worms, once thawed for 24 h at 4° C. in the presence of the extraction buffer (400 mM NaCl, 2.95 mM KCl, 32 mM $MgSO_4$, 11 mM $CaCl_2$, 50 mM Hepes, 5 mM ascorbic acid, 10 mM reduced glutathione, pH 7.5, filtered through 0.2 µm) in a proportion of 0.2 ml/g, are centrifuged (4500 g, 4° C., 15 min). The supernatant is recovered and the worm pellet is redispersed in 0.2 ml/g of extraction buffer and centrifuged again, this being carried out 4 times. The combined supernatants are filtered under pressure (2 bar) through a 5 µm filter and then a 0.1 µm filter (Pall filters).

The filtrate can be treated in two ways:

First method: the filtrate is diafiltered against 5 diavolumes of storage buffer (90 mM NaCl, 23 mM sodium gluconate, 27 mM sodium acetate, 5 mM KCl, 1.5 mM $MgCl_2$, 2.5 mM $CaCl_2$, pH 7.35, filtered through 0.2 µm) on a Pellicon XL-1000 kDa ultrafiltration cassette (Millipore), at 4° C. The retentate is finally concentrated on this same cassette to ~100 mg/ml before sterilizing filtration through a 0.2 µm filter and storage at −80° C.

Second method: the 5 µm filtrate is precipitated at the isoelectric point of *Arenicola marina* hemoglobin by adding 50% by volume of a 0.5N solution of sodium acetate/acetic acid, pH 4.15. After stirring for 30 minutes at 4° C., the solution is centrifuged (4500 g, 4° C., 15 min). The supernatant is removed and the pellet (containing the *Arenicola marina* hemoglobin) is washed twice against the same volume equivalent of ultrapure water (4500 g, 4° C., 5 min). The rinsed pellet is redispersed in the same volume equivalent of the storage buffer with stirring for 1 h at 4° C. The solution is centrifuged so as to remove the debris (4500 g, 4° C., 15 min). The supernatant is filtered under pressure through a 0.1 μm filter (Pall) and then diafiltered against 2 diavolumes on a Pellicon XL-1000 kDa cassette to a final concentration of ~100 mg/ml before sterilizing filtration through a 0.2 μm filter and storage at −80° C.

Example 2

Preparation of the Liquid Intermediate Composition

Two types of sodium alginate sold by Cargill: Satialgine™ US 61 and Satialgine™ US 551 EP were used. They conform to European pharmacopeia standards and are used as an additive, by way of a texturing: thickening and/or gelling agent, for many therapeutic applications.

They are used at a concentration of from 1 to 3% (w/v) depending on the type of application and the final texture desired. The sodium alginate powder is diluted, with magnetic stirring, in MilliQ (MQ) water to the desired concentration. The higher the alginate concentration, the more difficult it is to dissolve.

Furthermore, Satialgine™ US 551 EP is more viscous than Satialgine™ US 61. It is therefore sometimes necessary to heat (~50° C.) in order to improve the dissolution. Once the solution is homogeneous, after a few hours, it is cooled in ice, before adding the *Arenicola marina* hemoglobin thereto.

The *Arenicola marina* hemoglobin is prepared as described previously and stored at −80° C. before use, at a concentration of 100 mg/ml in a physiological buffer, termed storage buffer, which is calcium-free.

The *Arenicola marina* hemoglobin is thawed at 4° C. and dissolved in the sodium alginate solution at the concentration of 6 mg/ml. The solution is then homogenized with magnetic stirring.

Example 3

Preparation of the Dried Intermediate Composition

The solution obtained in example 2 is then dried under an air vacuum and in the presence of silica gel for between 12 and 24 h so as to obtain a dried intermediate composition.

Example 4

Polymerization

The dried intermediate composition, which is in the form of a thin film, is immersed in 10 ml of a 1% (w/v) solution of calcium chloride. The calcium solution is buffered with 10 mM Hepes (Sigma) at pH 7.0. This step enables the polymerization of the alginate solution and the immobilization of the *Arenicola marina* hemoglobin in the alginate matrix.

Several techniques were used to polymerize the solution of sodium alginate containing hemoglobin. Depending on the method used, it is possible to obtain various forms of dressing and therefore to envision the treatment of various types of wounds or of periodontal infections linked to the presence of anaerobic pathogens.

4.1: In Situ Polymerization

Double syringes (Plas-pak) are used for this application. One compartment of the syringe (A) is filled with a solution containing sodium alginate (Satialgine™ US 61) at 1% and hemoglobin at 5 mg/ml.

The other compartment (B) is filled with a 1% solution of $CaCl_2$ in a 10 mM Hepes buffer, pH 7.0.

Pressure exerted on the plunger makes it possible to bring the solutions of the two compartments into contact at the end (C) of the syringe and to polymerize the alginate in solution containing the hemoglobin (D).

4.2: Dialysis Polymerization

Figure 7:
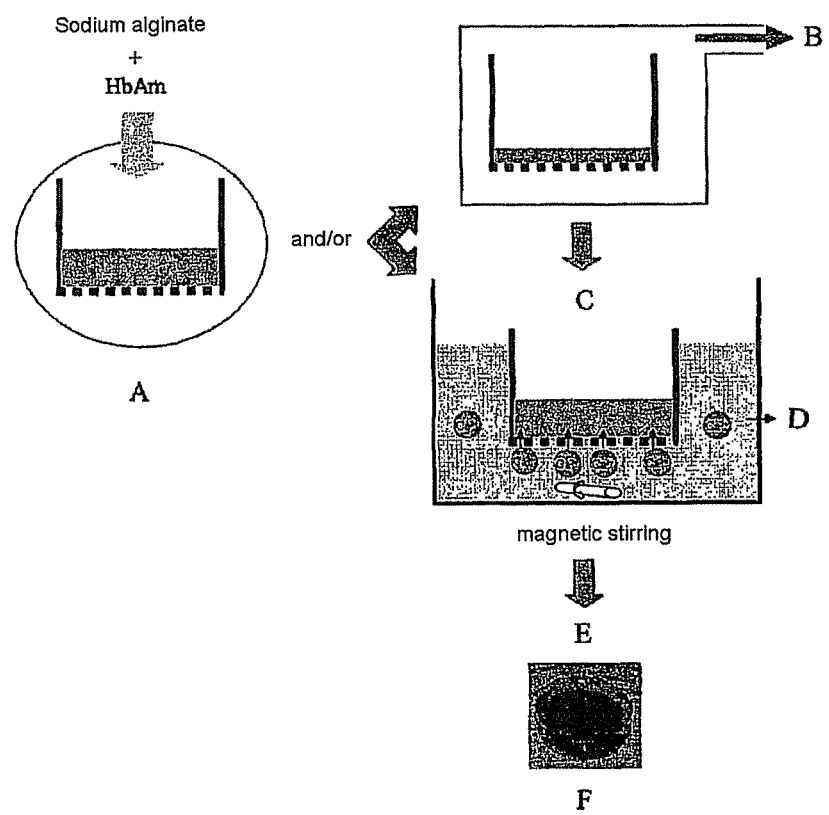
FIG. 7 represents the dialysis polymerization on a "Millipore" Minicell support.

The principle of the polymerization is shown in detail in FIG. 7.

The solution of sodium alginate containing the hemoglobin is deposited onto a porous membrane (A) (Minicell, 0.4 μm, Millipore) (HbAm=*Arenicola marina* hemoglobin).

The solution can be degassed and dried under vacuum and in the presence of silica gel (B), before polymerization, for between 12 h and 24 h, or polymerized as it is.

The polymerization is carried out by immersing the porous membrane (C) in a bath containing a solution containing 1% $CaCl_2$, 10 mM Hepes, pH 7.0, with stirring (D). The calcium diffuses through the membrane during the 12 h. The polymerization is carried out at 4° C.

Figure 3:
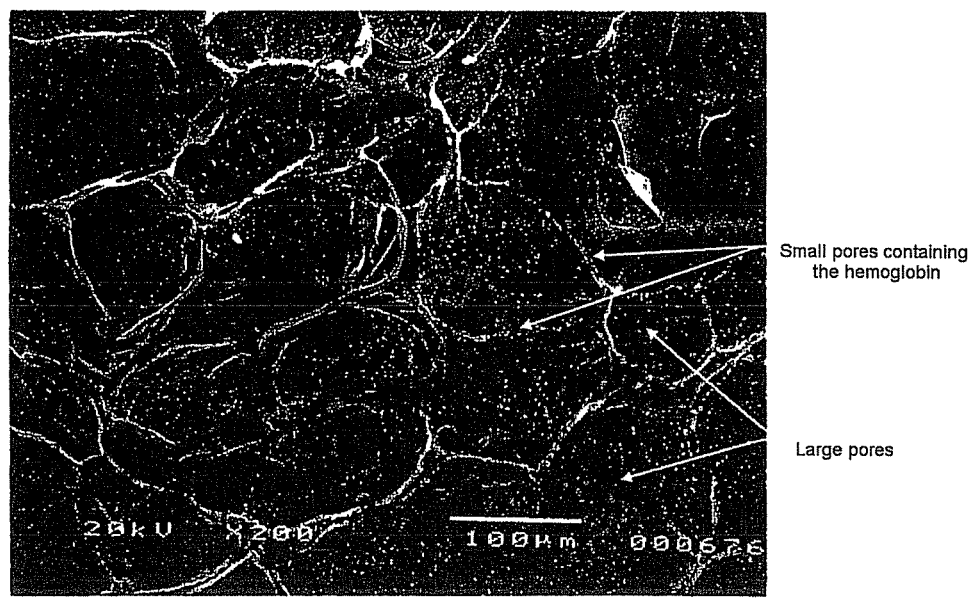
FIG. 3 represents the photograph of the scanning microscopy (JEOL JEM 1200EX) carried out on the external face of the matrix of calcium alginate containing *Arenicola marina* hemoglobin after gold shadowing. The resolution used here does not make it possible to visualize the hemoglobin.
Figure 4:
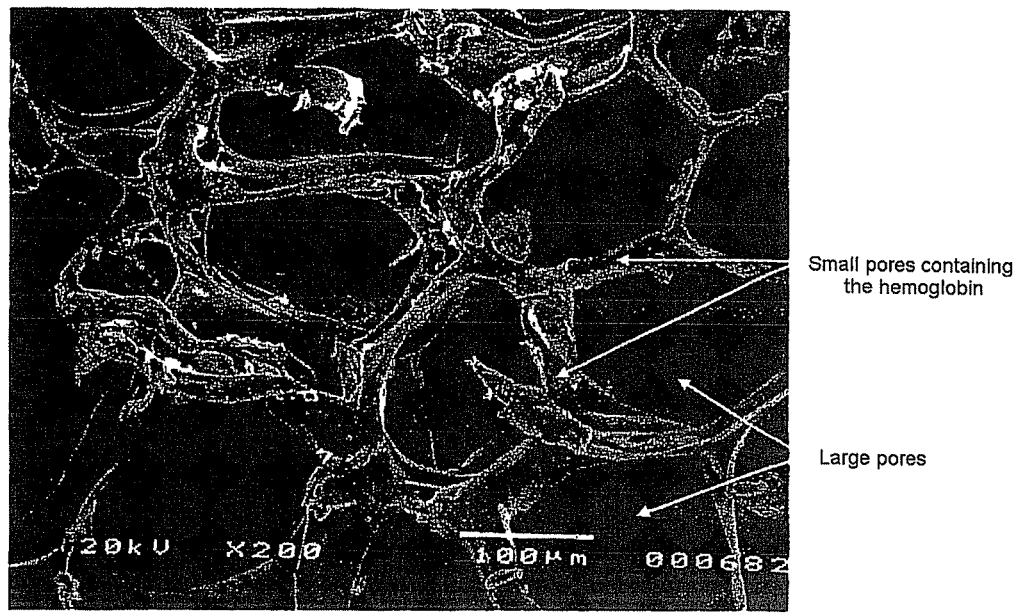
FIG. 4 represents the photograph of the scanning microscopy carried out on the internal face of the matrix of calcium alginate containing *Arenicola marina* hemoglobin (6 mg/ml) after gold shadowing and showing the porous appearance of the structure. The resolution used here does not make it possible to visualize the hemoglobin.
Figure 5:
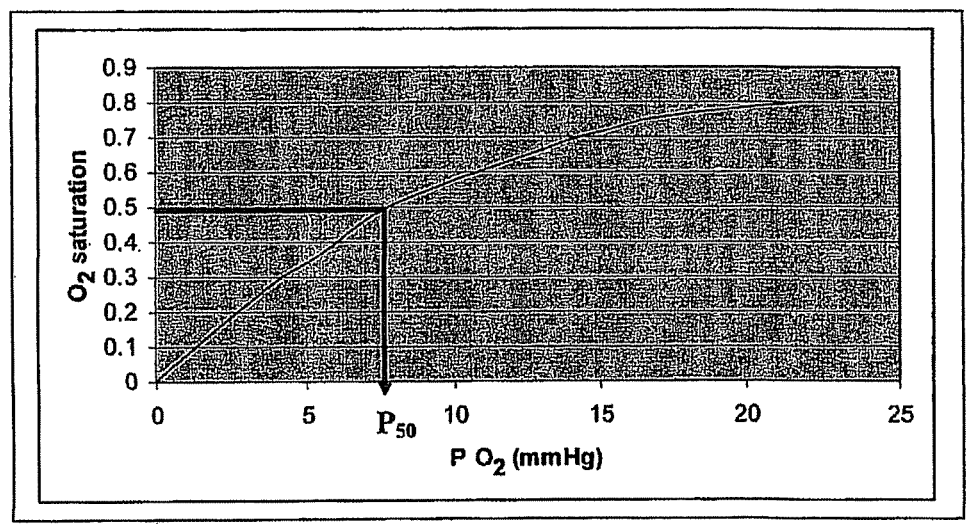
FIG. 5 shows a Barcroft representation (10 mg/ml *Arenicola marina* hemoglobin, 15% Ca, 1% sodium alginate, Hepes buffer, pH 7.35) for determining the $P_{50}$.
Figure 6:
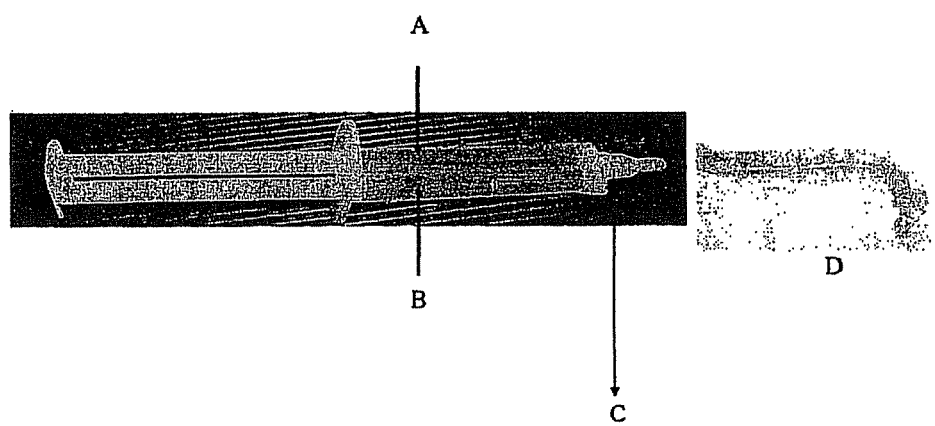
FIG. 6 represents a photograph of the syringe for producing a dressing in situ. The syringe is constituted of two compartments containing, firstly, the sodium alginate (Satialgine™ US 61) in aqueous solution with the hemoglobin and, secondly, an aqueous solution of calcium chloride for the polymerization of the alginate in situ, at the syringe outlet.

The polymer obtained is then thoroughly rinsed with MilliQ $H_2O$ (E) and then stored at 4° C. (F). The gel obtained was analyzed by scanning microscopy (FIGS. 3 and 4).

It is possible to dry the gel under vacuum by evaporation or by lyophilization, so as to conserve it and to rehydrate it before use (F).

4.3: Diffusion-Chamber Polymerization

Figure 8:
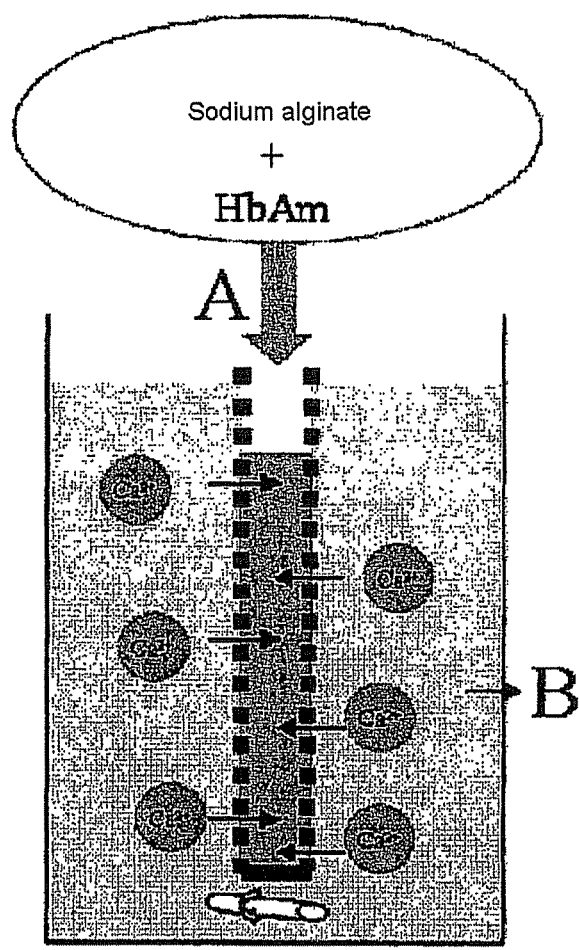
FIG. 8 represents the diffusion-chamber polymerization.

The polymerization (FIG. 8) takes place on either side of the aqueous solution of sodium alginate (1%) and of *Arenicola marina* hemoglobin (A) which is maintained between two porous membranes (1 μm) in a bath containing a solution containing 1% $CaCl_2$, 10 mM Hepes, pH 7.0, and with stirring (B).

Example 5

Hemoglobin Release

The dressing, prepared according to one of the methods described above, is immersed in 10 ml of a solution that is isoionic with respect to human blood (145 mM NaCl, 4 mM KCl, 2 mM $MgCl_2$, 10 mM Hepes, 2.5 mM $CaCl_2$, pH 7.35) and the whole is incubated at 34° C. in order to simulate the physiological medium of the wound.

At regular time periods, an amount of solution (0.5 ml) is removed in order to assay the released hemoglobin with Drabkin's reagent, reading being carried out on a spectrophotometer at 540 nm (colorimetric assay). The concentrations thus obtained in the volume of 0.5 ml are converted to a total amount of hemoglobin released by the dressing.

Figure 9:
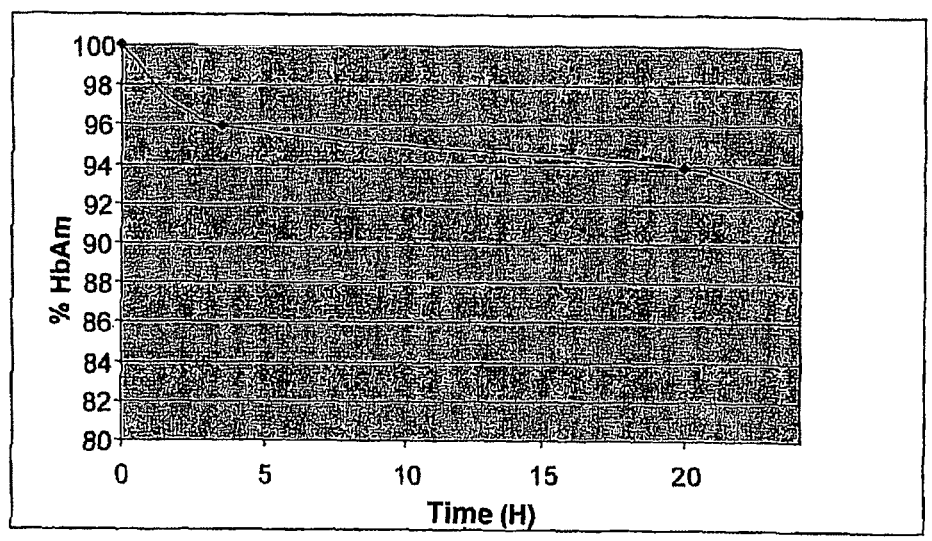
FIG. 9 represents the release of *Arenicola marina* hemoglobin (HbA) contained in a dressing prepared with Satialgine™ US551 alginate (Cargill) at 1% as a function of time.

FIG. 9 shows the results obtained:

After 4 h in solution, the dressing has released only 4% of hemoglobin.

After 20 h, the dressing has released only 6% of hemoglobin.

After 24 h, only 8% of the hemoglobin contained in the dressing has been released.

These three measurements confirm that the hemoglobin remains immobilized in the matrix for more than 24 hours.

An analysis of the structure of the hemoglobin released, by size exclusion chromatography (superose 6 column, 0.5 ml/min), was carried out. Samples were taken at various times (1 h30, 8 h and 24 h) and the optical density was measured at 280 nm and 414 nm (FIGS. 10, 11, 12).

Figure 10:
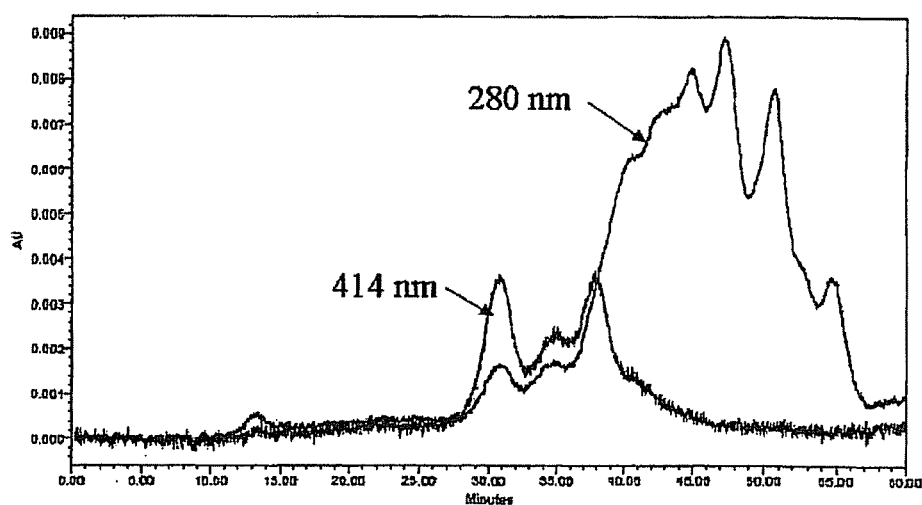
FIGS. 10, 11 and 12 represent HPLC chromatograms at two wavelengths (280 and 414 nm) obtained on samples taken, respectively, at 1 h30, 8 h and 24 h, from a solution which is isoionic with respect to human blood (see example 5) in which a dressing containing *Arenicola marina* hemoglobin has been placed.
Figure 11:
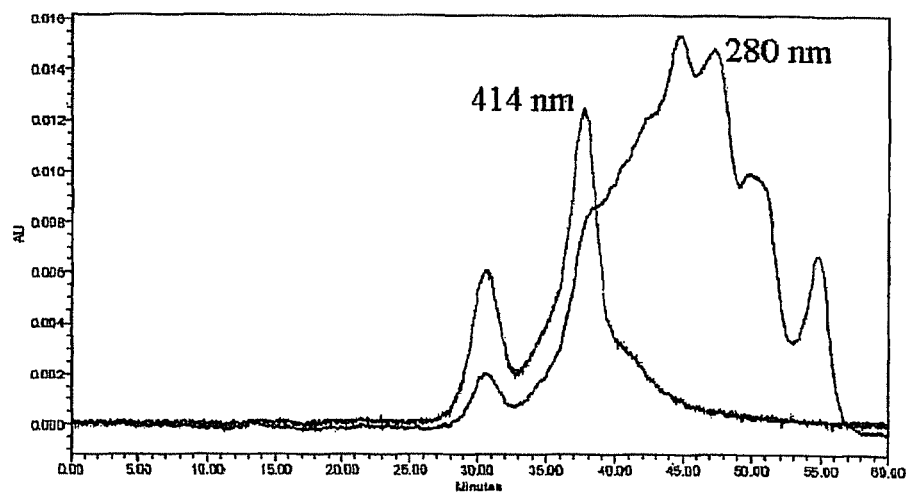
Figure 12:
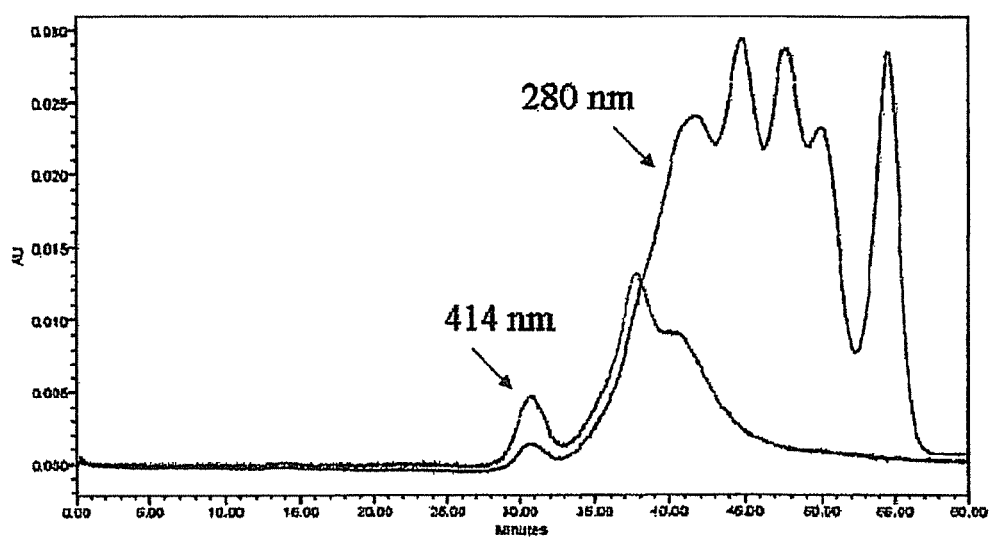

FIGS. 10, 11 and 12 give the chromatograms obtained and show that the hemoglobin released is a degraded hemoglobin (in dodecamer form, peak at 30 minutes), since the absorption peak for native hemoglobin, which is at 21 minutes, is non-existent.

Consequently, the small percentage of hemoglobin which is released (less than 10%) is degraded hemoglobin, thus confirming that the *Arenicola marina* hemoglobin remaining in the dressing is stable (otherwise it would be released).

Figure 13:
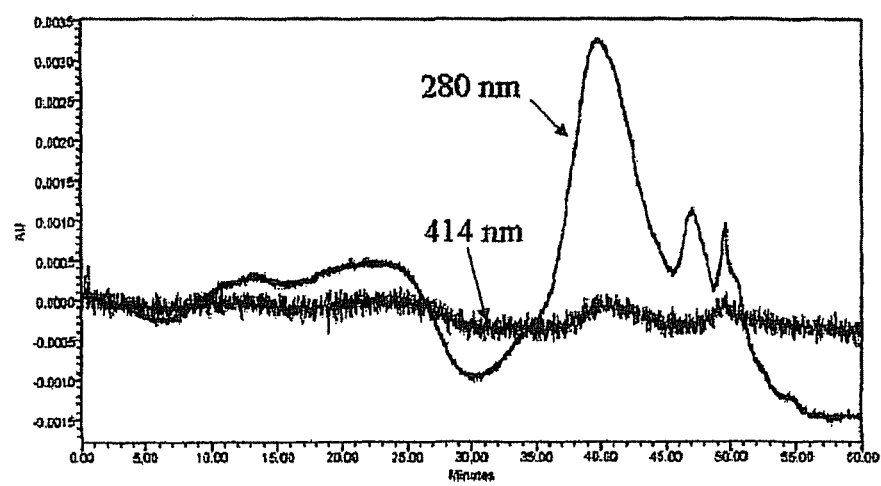
FIG. 13 represents the control HPLC chromatogram at the two wavelengths (280 and 414 nm), obtained with a dressing without hemoglobin at 24 h.

FIG. 13 gives the chromatogram obtained with a "control" dressing without hemoglobin, thus giving the absorption due only to the dressing.

Example 6

Comparison with the Preparation of application US2003/0180365

The preparation of application US2003/0180365 was prepared as described, by inserting therein 6 mg/ml of *Arenicola marina* hemoglobin.

The *Arenicola marina* hemoglobin release tests were carried out as described in example 5.

The formulation thus obtained has the appearance of a very viscous gel and, once immersed in the solution which is isoionic with respect to human blood, as described in example 5, complete liquefaction of the gel after 12 h and therefore total release of the *Arenicola marina* hemoglobin are observed.

The invention claimed is:

1. A composition comprising extracellular Annelid hemoglobin, immobilized in a divalent cation- or trivalent cation-gelled physiologically compatible polysaccharide network, wherein the composition is in the form of a dressing, and has a water content of from 0% to 98% and pores of from 2 nm to 1 µm; and about 0.1% (w/w) to about 60% (w/w) of the Annelid hemoglobin based on the total dry weight of the Annelid hemoglobin and network.

2. A composition according to claim 1, wherein the amount of the Annelid hemoglobin, relative to the total dry weight of the Annelid hemoglobin and of network, is from 15% (w/w) to 45% (w/w).

3. A composition according to claim 1, wherein the percentage water content is from 95% to 98%.

4. A composition according to claim 1, wherein the percentage water content is less than 5%.

5. A composition according to claim 1, wherein the Annelid hemoglobin is chemically modified or crosslinked.

6. A composition according to claim 1, wherein the polysaccharide is selected from chitosan, carrageenans, carboxymethylcellulose and alginates.

7. A composition according to claim 1, wherein the divalent cation- or trivalent cation-gelled physiologically compatible polysaccharide is calcium alginate.

* * * * *